(12) United States Patent
Li et al.

(10) Patent No.: US 12,384,752 B2
(45) Date of Patent: Aug. 12, 2025

(54) TRIAZOLYL CROSS-LINKING AGENT AS WELL AS PREPARATION METHOD AND USE THEREOF

(71) Applicant: POME TECHNOLOGY CO., LTD., Liaocheng (CN)

(72) Inventors: Mingxin Li, Liaocheng (CN); Xiuting Men, Liaocheng (CN); Congcong Gong, Liaocheng (CN); Ke Wang, Liaocheng (CN)

(73) Assignee: POME TECHNOLOGY CO., LTD., Liaocheng (CN)

( * ) Notice: Subject to any disclaimer, the term of this patent is extended or adjusted under 35 U.S.C. 154(b) by 0 days.

(21) Appl. No.: 18/843,302

(22) PCT Filed: Apr. 29, 2022

(86) PCT No.: PCT/CN2022/090550
§ 371 (c)(1),
(2) Date: Sep. 2, 2024

(87) PCT Pub. No.: WO2023/165011
PCT Pub. Date: Sep. 7, 2023

(65) Prior Publication Data
US 2025/0109111 A1    Apr. 3, 2025

(30) Foreign Application Priority Data
Mar. 3, 2022  (CN) .......................... 202210203306.1

(51) Int. Cl.
*C07D 249/14* (2006.01)
*C07D 403/14* (2006.01)
*C08G 73/12* (2006.01)
*C08K 5/3445* (2006.01)

(52) U.S. Cl.
CPC ......... *C07D 249/14* (2013.01); *C07D 403/14* (2013.01); *C08K 5/3445* (2013.01); *C08G 73/12* (2013.01)

(58) Field of Classification Search
CPC ..... C07D 403/14; C08K 5/3445; C08G 73/12
See application file for complete search history.

(56) References Cited

U.S. PATENT DOCUMENTS 8,871,870 B2 * 10/2014  He ....................... C09D 147/00
                                                        525/232

FOREIGN PATENT DOCUMENTS

| CN | 102375336 B  | 10/2013 |
|----|--------------|---------|
| CN | 104093779 A  | 10/2014 |
| CN | 109478016 A  | 3/2019  |
| CN | 111690247 A  | 9/2020  |
| CN | 112442063 A  | 3/2021  |
| CN | 113980272 A  | 1/2022  |
| JP | 5446203 B2   | 3/2014  |
| KR | 20210022411 A | 3/2021 |
| TW | 201235781 A  | 9/2012  |

OTHER PUBLICATIONS

R. Arif, et al., Synthesis, Characterization, DNA Binding, Antibacterial, and Antioxidant Activity of New Bis-phthalimides, Russian Journal of General Chemistry, 2016, pp. 1374-1380, vol. 86 No. 6.

* cited by examiner

*Primary Examiner* — Rebecca L Anderson
(74) *Attorney, Agent, or Firm* — Bayramoglu Law Offices LLC

(57) ABSTRACT

A cross-linking agent as well as a preparation method and the use thereof is disclosed. The structure of the cross-linking agent contains a triazolyl, and contains a double bond, an amide acid, or an imide structure at the same time. The cross-linking agent is added into a resin composition, so that the film-forming property can be improved, the adhesion between the cured resin and a copper or copper alloy base material is improved, the discoloration of the copper or copper alloy base material is inhibited, and meanwhile, the resin has better heat resistance and chemical resistance after curing. The problem of poor compatibility caused by excessive additive types is avoided, and meanwhile, the problem of excessive additives may be relieved.

18 Claims, No Drawings

TRIAZOLYL CROSS-LINKING AGENT AS WELL AS PREPARATION METHOD AND USE THEREOF

CROSS REFERENCE TO THE RELATED APPLICATIONS

This application is the national phase entry of International Application No. PCT/CN2022/090550, filed on Apr. 29, 2022, which is based upon and claims priority to Chinese Patent Application No. 202210203306.1, filed on Mar. 3, 2022.

TECHNICAL FIELD

The present application relates to a triazolyl cross-linking agent as well as a preparation method and use thereof, which belongs to the field of cross-linking agent.

BACKGROUND

In recent years, polyimide and polybenzoxazole resins, which have excellent heat resistance and mechanical properties, have been widely used as insulation materials for electronic components and as passivation films, surface protection films, and interlayer insulation films for semiconductor devices. By coating, exposing, developing, and curing the photosensitive polyimide resin or polybenzoxazole resin compositions, relief patterned film with good heat resistance can be obtained. For positive photosensitive resin compositions based on polybenzoxazole resins, not only can a microfine pattern be formed, but the oxazole ring formed after curing is also endowed with good heat resistance. When using resin composites for semiconductor and other applications, the physical properties of the heat-cured film are important because the film will remain in the device as a permanent film. For example, in order to enhance the reliability of semiconductor packaging, the film and the surface material of the semiconductor chip should have a high degree of adhesion. However, for the resin compositions described above, especially for resin-cured films formed from positive photosensitive resin compositions capable of forming microfine patterns, the presence of a variety of additives, such as photosensitizers and sensitizers, in the constituent compositions results in a lower adhesion strength than in the case of fewer additives.

On the other hand, with the development of semiconductor device integration and chip size miniaturization, the wiring method of semiconductor devices as well as the installation method have changed. For example, the wiring is changed from the previous gold or aluminum wiring to lower resistance copper or copper alloy wiring, and the installation method is changed from the previous lead-tin eutectic soldering to higher density installation of ball grid arrays and chip size installation. The cured resin film is in direct contact with the copper or copper alloy and the solder bumps, which requires a good adhesion between the resin film and the copper or copper alloy base material, good chemical resistance, and high heat resistance of the cured resin film, while not causing discoloration of the copper or copper alloy base material.

In the prior art, a variety of additives are usually added to the resin to obtain good resin-cured film properties. In patent CN109478016A, the adhesion of the resin to the substrate is increased by adding nitrogen-containing aromatic compounds. In patent JP5446203B2, the addition of heterocyclic compounds is used to reduce the corrosion of the resin on copper or copper alloys and to increase the adhesion. In patent CN102375336B, purine derivatives, cross-linking agents, and organotitanium compounds are added to increase the adhesion, heat resistance, chemical resistance, and inhibit discoloration of copper or copper alloy substrates. In order to achieve the comprehensive performance, a variety of additives are added in the prior art, which often results in an excessive content of additives, which in turn reduces the performance of the resin material. In addition, the presence of a variety of additives often has the problem of whether the cooperativeness is matched, otherwise, it is easy to improve performance of one aspect while causing a decrease in another.

SUMMARY

According to a first aspect of the present application, there is provided a triazolyl cross-linking agent, where the triazolyl cross-linking agent has a general formula described in Formula I:

W is an organic group shown in general formula (6) or (7):

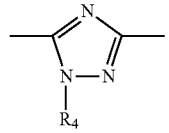

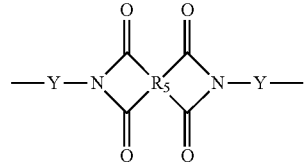

in the general formula (7), Y represents a structure shown in the general formula (6);

$R_4$ is a hydrogen atom or a hydrocarbon group with a carbon atom number of 1 to 10;

$R_5$ is an organic group with a carbon atom number of 4 to 40;

$X_1$ and $X_2$ are any one independently selected from the group consisting of structures described in formulae (2), (3), (4), and (5)

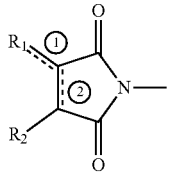

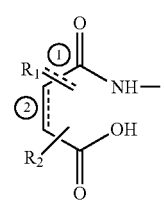

(4)

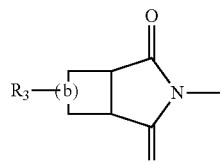

(5)

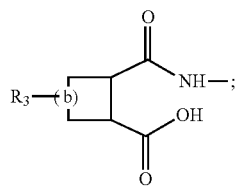

In the formulae (2) and (3), ==== represents that positions ① or ② are both single bonds or one of them is a double bond; when both are single bonds, $R_1$ is an organic group containing a carbon-unsaturated double bond with a carbon atom number of 2 to 10, and R2 is a hydrogen atom or an organic group with a carbon atom number of 1 to 6; when position ① is a double bond, $R_1$ is an alkylidene group with a carbon atom number of 1 to 3, and $R_2$ is a hydrogen atom or an organic group with a carbon atom number of 1 to 6; when position ② is a double bond, $R_1$ and $R_2$ are independently a hydrogen atom or a hydrocarbon group with a carbon atom number of 1 to 3, respectively;

in the formulae (4) and (5), $R_3$ is an organic group containing a carbon-unsaturated double bond with a carbon atom number of 2 to 10, and (b) is an aliphatic ring with a carbon atom number of 4 to 8; or $R_3$ is a hydrogen atom, a methyl group, or an ethyl group, and (b) is an aliphatic ring with a carbon atom number of 4 to 8 containing a carbon-unsaturated double bond in the ring.

Specifically, the cross-linking agent can be a single type of structure or a mixture of two or more structures:

(1-1)

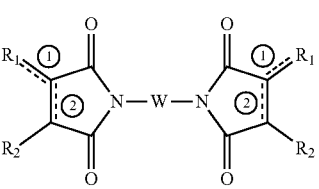

(1-2)

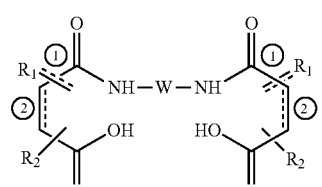

(1-3)

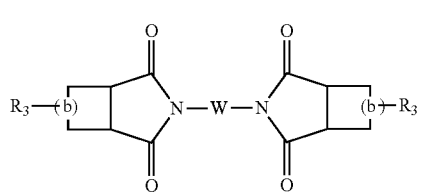

(1-4)

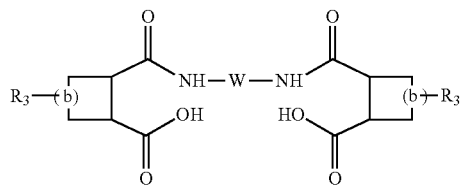

W is any of the structure shown in the general formulae (6) and (7). Specifically, W can be the structure shown in the general formula (6) or the structure shown in the general formula (7).

In the formulae (2) and (3), $R_1$ and $R_2$ are substituents, and ==== represents that positions ① or ② are both single bonds or one of them is a double bond. To facilitate further explanation, the location of the double bond is illustrated below in three categories, i.e., positions ① and ② are both single bonds; position ① is a double bond, and position ② is a single bond; position ① is a single bond, and position ② is a double bond. When positions ① and ② are both single bonds, $R_1$ is an organic group containing a carbon-unsaturated double bond with a carbon atom number of 2 to 10, and $R_2$ is a hydrogen atom or an organic group with a carbon atom number of 1 to 6. In the present invention, the organic group can be a hydrocarbon group such as alkyl, alkenyl, alkynyl, alkylene, cycloalkyl, aromatic, arylalkyl, etc., or other organic groups containing a heteroatom such as N, O, and S, etc. For example, $R_1$ can be vinyl, propenyl, allyl, 1-methyl-1-vinyl, or 1-buten-4-yl, 1-penten-5-yl, preferably $R_1$ is vinyl or allyl; $R_2$ can be a hydrogen atom, an alkyl group such as methyl, ethyl, propyl, butyl, pentyl, hexyl, isopropyl, tert-butyl, etc., a cycloalkyl group such as cyclopentyl and cyclohexyl, etc., a group containing an unsaturated double bond such as vinyl, propenyl, allyl, and butenyl, etc., and a benzene ring, or a hydrocarbon group containing a heteroatom such as N, O, and S, etc.; preferably, $R_2$ is a hydrogen atom, a methyl, an ethyl, or a propyl.

When position ① is a double bond, $R_1$ is connected to the main chain structure by a double bond, $R_1$ is an alkylidene group with a carbon atom number of 1 to 3, and $R_2$ is a hydrogen atom or an organic group with a carbon atom number of 1 to 6. For example, $R_1$ can be methylene, ethylene, propylene; preferably, $R_1$ is a methylene; $R_2$ can be a hydrogen atom, an alkyl group such as methyl, ethyl, propyl, butyl, pentyl, hexyl, isopropyl, tert-butyl, etc, a cycloalkyl group such as cyclopentyl and cyclohexyl, etc, a group containing an unsaturated double bond such as vinyl, propenyl, allyl, and butenyl, etc, and a benzene ring, or a hydrocarbon group containing a heteroatom such as N, O, and S, etc; preferably, $R_2$ is a hydrogen atom, a methyl, an ethyl, or a propyl.

When position ② is a double bond, in order to ensure the reactivity of the double bond and to reduce the steric hindrance, the substituents $R_1$ and $R_2$ should be small volume functional groups as much as possible. $R_1$ and $R_2$ are independently a hydrogen atom or a hydrocarbon group with a carbon atom number of 1 to 3, respectively, which may be the same or different, and which can be a hydrogen atom, an alkyl group such as methyl, ethyl, propyl, etc., or an alkenyl group such as vinyl, allyl, etc.; preferably, $R_1$ and $R_2$ are independently a hydrogen atom or a methyl, respectively. It is worth noting that, when a double bond is present at position ① or ②, without affecting structural stability, double bonds can also exist in the substituents $R_1$ and $R_2$, which is not limited by the present invention.

Formula (3) is an asymmetric structure; when position ① is a double bond, i.e., the substituent $R_1$ is connected to the main chain by a double bond, the connection position between the double bond and the main chain is not fixed, and its neighboring group can be a —CONH— group or a —COOH group. When position ① is a single bond, the substituent positions of the substituents $R_1$ and $R_2$ are not fixed, and when one of them is adjacent to a —CONH— group, the other is adjacent to a —COOH group, and vice versa.

In the formulae (4) and (5), $R_3$ is an organic group containing a carbon-unsaturated double bond with a carbon atom number of 2 to 10, and (b) is an aliphatic ring with a carbon atom number of 4 to 8. For example, $R_3$ can be vinyl, propenyl, allyl, 1-methyl-1-vinyl, or 1-buten-4-yl, 1-penten-5-yl; preferably, $R_3$ is vinyl or allyl; (b) can be cyclobutyl, cyclobutenyl, cyclopentyl, cyclohexyl, 1-alkeno-cyclohexyl, and the like. It is worth noting that, when the substituent $R_3$ contains carbon unsaturated double bonds, the (b) structure can also contains double bonds, for example, it can be 5-allyl nadic anhydride.

In the formulae (4) and (5), $R_3$ is a hydrogen atom, a methyl group, or an ethyl group, and (b) is an aliphatic ring with a carbon atom number of 4 to 8 containing a carbon-unsaturated double bond in the ring. For example, (b) can list the structures shown in (I) below. In this case, it is the double bond on the ring that acts as the cross-linking agent, and cross-linking can be carried out by undergoing a free radical chain addition reaction.

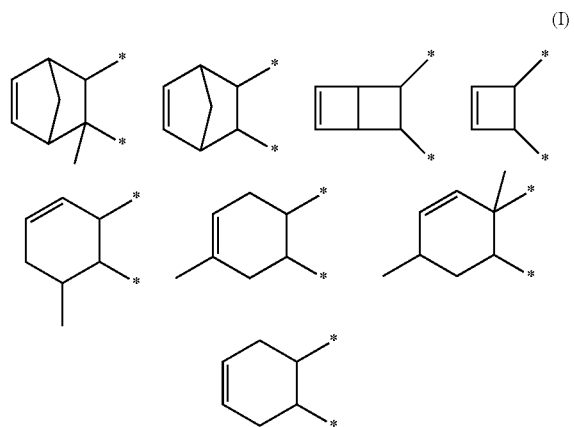

(I)

In the general formula (6), $R_4$ is a hydrogen atom or a hydrocarbon group with a carbon atom number of 1 to 10. For example, $R_4$ can be a hydrogen atom, an alkyl group such as methyl, ethyl, propyl, isopropyl, butyl, tert-butyl, pentyl, hexyl, heptyl, octyl, nonyl, decyl, etc., a cycloalkyl group such as cyclopentyl, cyclohexyl, etc., an aromatic group such as phenyl and tolyl, an arylalkyl group such as benzyl, phenethyl, phenylpropyl, etc., or an unsaturated alkenyl group such as vinyl, allyl, butenyl, propenyl, isopropenyl, styryl, etc., preferably a hydrogen atom or an alkyl group, more preferably a hydrogen atom or an alkyl group with a carbon atom number of 1 to 3, more preferably a hydrogen atom, a methyl or an ethyl.

In the general formula (7), Y represents a structure shown in the general formula (6), and $R_5$ is an organic group with a carbon atom number of 4 to 40.

Y represents a structure shown in the general formula (6). Since there is a substituent $R_4$ in the general formula (6), depending on the position of $R_4$, the structure of the general formula (7) has three isomers as shown in (II) below:

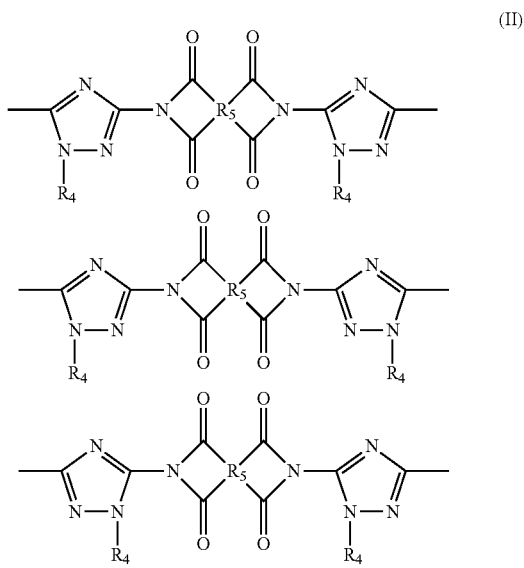

(II)

$R_5$ is an organic group with a carbon atom number of 4 to 40; further preferably an organic group with a carbon atom number of 6 to 40 containing an aromatic ring. For example, it can be the structure shown in formula (III) below, but is not limited to these.

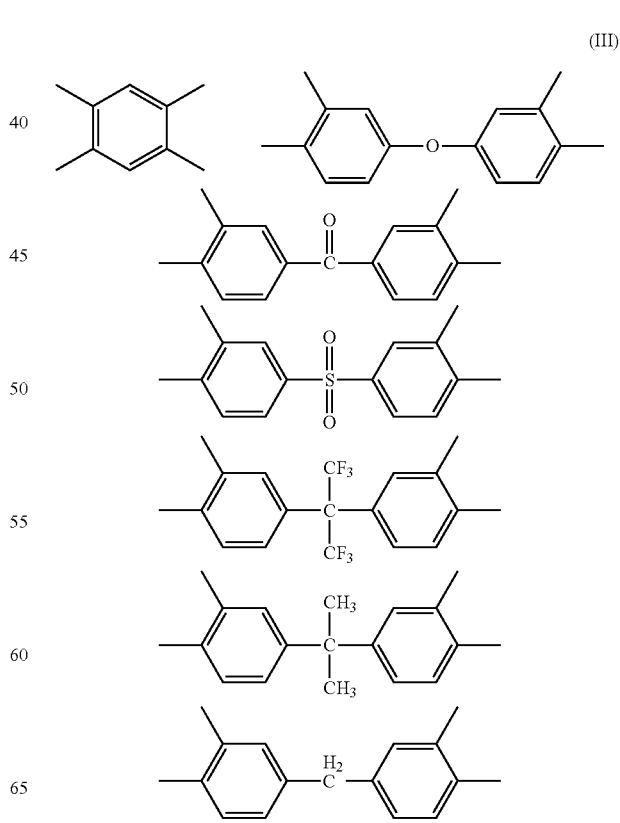

(III)

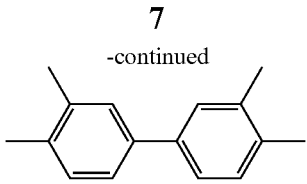

Compared to the structure shown in the general formula (6), when the cross-linking agent contains the structure shown in the general formula (7), the cross-linking agent containing the structure shown in the general formula (7) has a smaller number of carbon-carbon double bonds for the crosslinking reaction, and the number of triazolyl groups is comparable or less, for the same parts by weight of the cross-linking agent. Therefore, selective adjustments can be made according to the needs during use.

Optionally, $X_1$ and $X_2$ have the same structure.

Optionally, a compound of formula (2) is any one selected from the group consisting of (9), (11), and (13);

a compound of formula (3) is any one selected from the group consisting of (8), (10), and (12);

a compound of formula (4) is (14);

a compound of formula (5) is (15).

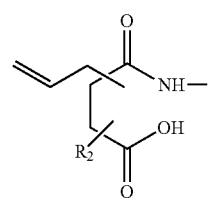
(8)

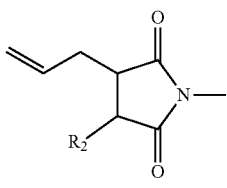
(9)

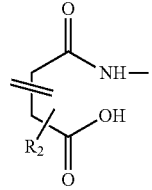
(10)

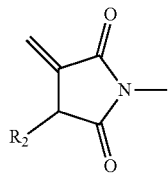
(11)

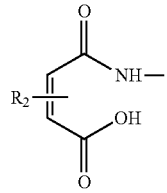
(12)

(13)

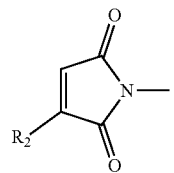
(14)

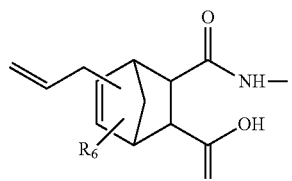
(15)

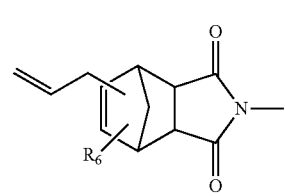

In formulae (8) to (11), $R_2$ is a hydrogen atom or an organic group with a carbon atom number of 1 to 6;

in formulae (12) to (13), $R_2$ is a hydrogen atom or a hydrocarbon group with a carbon atom number of 1 to 3;

in formulae (14) to (15), $R_6$ is a hydrogen atom or an organic group with a carbon atom number of 1 to 6.

From the perspective of reaction activity, if $R_2$ is a small volume group, it can reduce steric hindrance, enhance the collision probability of double bonds in allyl groups, and thus enhance reaction activity. From the perspective of the effect on the resin-cured film after cross-linking and curing, if $R_2$ has a longer chain segment, it can avoid cross-linking too densely to a certain extent, and reduce the volumetric shrinkage of the resin after curing.

In formulae (12) to (13), $R_2$ is a hydrogen atom or a hydrocarbon group with a carbon atom number of 1 to 3; preferably a hydrogen atom or an alkyl group; further preferably a hydrogen atom or a methyl.

In formulae (14) to (15), $R_6$ is a hydrogen atom or an organic group with a carbon atom number of 1 to 6, and the definition of $R_6$ is consistent with the definition of $R_2$ in formulas (8) to (11). Preferably, $R_6$ is a hydrogen atom. In addition, the substitution positions of the allyl and $R_6$ on the ring can be any one of positions 1, 4, 5 and 6 on the ring and are not limited herein.

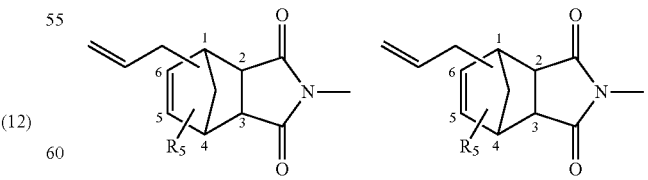
(IV)

Further, in the general formulae (6) and (7), $R_4$ is a hydrocarbon group with a carbon atom number of 1 to 3.

Further, in the general formulae (6) and (7), $R_4$ is an alkyl group with a carbon atom number of 1 to 3, preferably methyl or methyl.

Optionally, a structure of the cross-linking agent includes at least one of (16) to (25):

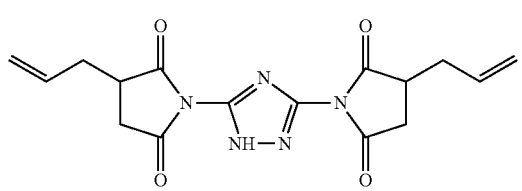
(16)

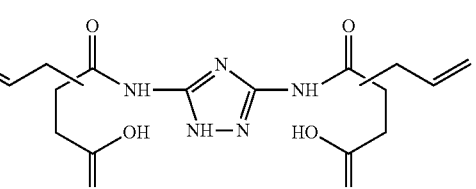
(17)

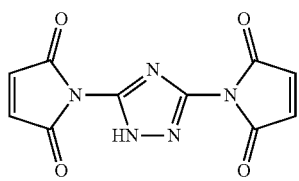
(18)

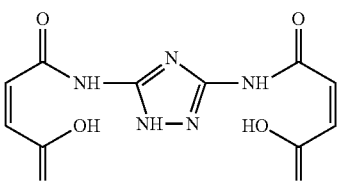
(19)

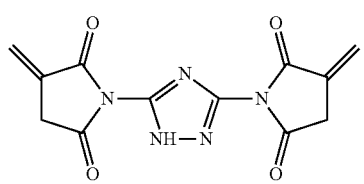
(20)

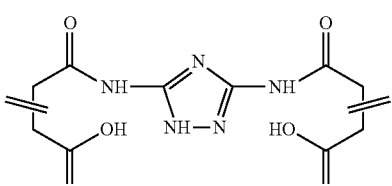
(21)

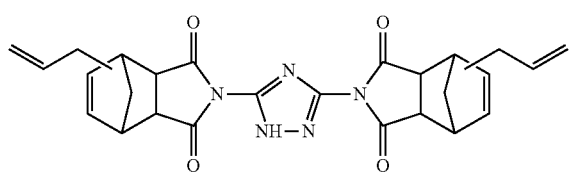
(22)

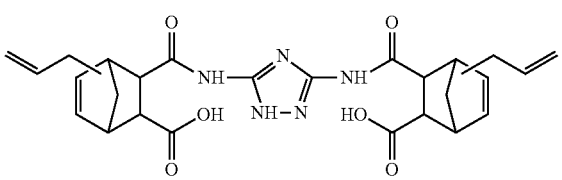
(23)

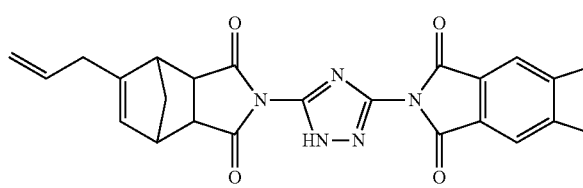
(24)

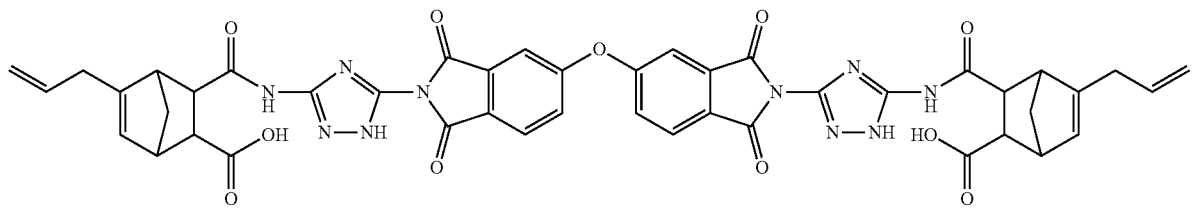
(25)

Optionally, when positions ① and ② are both C—C bonds, $R_1$ is selected from organic groups of $C_2$-$C_{10}$ containing unsaturated double bonds, and $R_2$ is selected from a hydrogen atom or organic groups of $C_1$-$C_6$, or:

when position ① is a C=C bond, $R_1$ is selected from alkylene groups of $C_1$-$C_3$, and $R_2$ is selected from a hydrogen atom or organic groups of $C_1$-$C_6$, or:

when position ② is a C=C bond, $R_1$ and $R_2$ are independently selected from a hydrogen atom or hydrocarbon groups of $C_1$-$C_3$, respectively;

when $R_3$ is selected from organic groups of $C_2$-$C_{10}$ containing a carbon unsaturated double bond, (b) is selected from aliphatic ring of $C_4$-$C_8$; when $R_3$ is one selected from the group consisting of a hydrogen atom, methyl, and ethyl, (b) is selected from aliphatic ring of $C_4$-$C_8$ containing a carbon-unsaturated double bond in the ring;

$R_4$ is a hydrogen atom or a hydrocarbon group with a carbon atom number of 1 to 10.

The present application designs and synthesizes a triazolyl cross-linking agent by simultaneously introducing a double bond, an amide acid or imide structure, and a triazolyl group into the structure, and by adding it to a resin composition, not only can it improve film-forming properties, improve the adhesion of the resin to the copper or copper alloy substrate after curing, and inhibit the discoloration of the copper or copper alloy substrate, but also the resin has a better heat resistance and chemical resistance after curing. It avoids the poor compatibility caused by too many types of additives, and at the same time alleviate the problem of excessive additives.

According to a second aspect of the present application, there is provided a preparation method of the triazolyl cross-linking agent above, where a reaction step comprises:

performing an amidation reaction between an anhydride monomer of the structure shown in either formula (26) or (27) and a diamine monomer of the structure shown in formula (28) to obtain the triazolyl cross-linking agent; or performing an amidation reaction between an anhydride monomer of the structure shown in either formula (26) or (27) and a diamine monomer of the structure shown in formula (28), followed by an imidization reaction to obtain the triazolyl cross-linking agent;

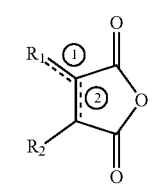

(26)

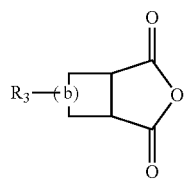

(27)

$H_2N-W-NH_2$ (28)

in the formulae (26) to (28), $R_1$, $R_2$, $R_3$, (b), ==== and W are defined as described above.

By controlling the amount and order of addition of anhydride monomers with the structure shown in formula (26) or (27), as well as the reaction sequence of amidation and imidization, compounds with the same or different $X_1$ and $X_2$ in the same cross-linking agent structure can be obtained. In the case where $X_1$ and $X_2$ are the same, for example, the anhydride monomer with the structure shown in formula (26) or (27) undergoes an amidation reaction with a diamine monomer shown in formula (28) to obtain a polyamide acid compound, which is a triazolyl cross-linking agent with a structure shown in formula (1-2) or (1-4). The anhydride monomer with the structure shown in formula (26) or (27) undergoes an amidation reaction with a diamine monomer shown in formula (28) followed by an imidization reaction to obtain a triazolyl cross-linking agent with a structure shown in formula (1-1) or (1-3). For the amidation reaction followed by an imidization reaction, if the imidization reaction is incomplete, a mixture of triazolyl cross-linking agents with the structures shown in formulae (1-1) and (1-2), or a mixture of triazolyl cross-linking agents with the structures shown in formulae (1-3) and (1-4) can be obtained. The product of the incomplete imidization reaction is also within the scope of protection of the present invention.

In the case where $X_1$ and $X_2$ are different, for example, by controlling the addition amount of the anhydride monomer with the structure shown in formula (26), a compound with the structure shown in formula (1-5) is firstly obtained by carrying out an amidation reaction and an imidization reaction between an anhydride monomer with the structure shown in formula (26) and a diamine monomer with the structure shown in formula (28), and then it undergoes an amidation reaction with the compound with the structure shown in formula (26) to obtain a triazolyl cross-linking agent with the structure shown in formula (1-6).

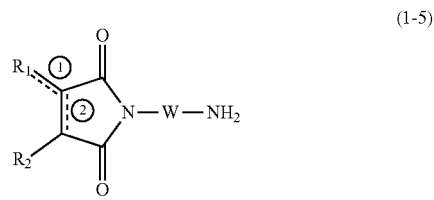

(1-5)

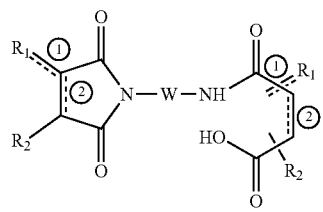

(1-6)

After the amidation reaction or imination reaction, it further includes a step of post-treating the reaction solution to obtain the cross-linking agent product shown in formula (1). For example, in the case of $X_1$ and $X_2$ being the same, after the amidation reaction, the reaction solution is directly post-treated to obtain the amide acid compound, i.e., the cross-linking agent shown in formula (1-2) or (1-4); after the amidation reaction, the obtained reaction solution is further subjected to an imidization reaction, and after the amination reaction is completed, post-treatment is carried out on the obtained reaction solution to obtain the cross-linking agent shown in formula (1-1) or (1-3). The post-treatment of the reaction solution is a means of purifying compounds common in the art and presents no difficulty to those skilled in the art. For example, the post-treatment includes a step of removing solvents and other impurities by means of distillation or vacuum distillation, thereby obtaining the product; or water can be added to the reaction solution so that the product precipitates directly. Therein, the main components of the impurities are unreacted raw materials as well as by-products formed by the reaction.

Optionally, the amidation reaction and the imidization reaction need to be carried out in an aprotic polar solvent.

Optionally, the aprotic polar solvent is at least one selected from the group consisting of N-methylpyrrolidone, N,N-dimethylformamide, N,N-dimethylacetamide, dimethylsulfoxide, and γ-butyrolactone.

Optionally, a temperature of the amidation reaction and the imidization reaction is independently in a range from 0° C. to 100° C.

Optionally, a temperature of the amidation reaction and the imidization reaction is independently in a range from 20° C. to 50° C.

Optionally, the temperature of the reactions are independently selected from any value or a range value determined by any two of 0° C., 10° C., 20° C., 25° C., 30° C., 35° C., 40° C., 50° C., 60° C., 70° C., 80° C., 90° C., 100° C.

Optionally, a time of the amidation reaction and the imidization reaction is independently in a range from 10 h to 40 h.

Optionally, a time of the amidation reaction and the imidization reaction is independently in a range from 15 h to 30 h.

Optionally, the reaction time can be independently selected from any value or a range value determined by any two of 10 h, 15 h, 20 h, 25 h, 30 h, 35 h, 40 h.

Optionally, a molar ratio of the anhydride monomer to the diamine monomer is 2: (0.9-1.1).

Optionally, a molar ratio of the anhydride monomer to the diamine monomer is 2:1.

Optionally, when an amidation reaction followed by an imidization reaction is adopted:
the amidation reaction is followed by adding base and anhydride to the reaction solution, and then the imidization reaction is carried out.

Optionally, the base is at least one selected from the group consisting of pyridine, triethylamine, and diisopropylethylamine.

Optionally, the anhydride is at least one selected from the group consisting of acetic anhydride, and trifluoroacetic anhydride.

Specifically, after the amidation reaction, base and anhydride are directly added to the reaction solution, and an amide acid compound obtained from the amidation reaction is then subjected to the imidization reaction to obtain a cross-linking agent containing an imide ring structure. The base can be any base reported in the prior art that can be used to catalyze the imidization, such as pyridine, triethylamine or diisopropylethylamine, etc., preferably pyridine, and the amount of the base is two or more times the molar amount of the anhydride monomers shown in formula (26) or (27), for example, 2-10 times, i.e., it can be 2 times, 3 times, 4 times, 5 times, 6 times, 7 times, 8 times, 9 times, or 10 times. The anhydride used may be any anhydride reported in the prior art that can be used for imidization, such as acetic anhydride, trifluoroacetic anhydride, etc., preferably acetic anhydride. The amount of the anhydride is 2 times and more, e.g. 2 to 10 times, the molar amount of the anhydride monomer shown in the general formula (26) or (27), for example it can be 2 times, 3 times, 4 times, 5 times, 6 times, 7 times, 8 times, 9 times, 10 times.

According to a third aspect of the present application, there is provided a resin composition.

A resin composition, where the resin composition comprises a heat-resistant resin and a triazolyl cross-linking agent, and the triazolyl cross-linking agent is the triazolyl cross-linking agent as described above and/or the triazolyl cross-linking agent obtained by the preparation method as described above.

Optionally, in the resin composition, each 100 parts of the heat-resistant resin corresponds to 0.5 to 50 parts of the triazolyl cross-linking agent by mass.

Optionally, in the resin composition, each 100 parts of the heat-resistant resin corresponds to 5 to 40 parts of the triazolyl cross-linking agent by mass.

Optionally, in the resin composition, each 100 parts of the heat-resistant resin corresponds to 8 to 30 parts of the triazolyl cross-linking agent by mass.

Relative to 100 mass parts of resin, the amount of the triazolyl cross-linking agent of the present application is 0.5-50 parts by mass. In order to balance heat resistance, chemical resistance, and adhesion, the content of the triazolyl cross-linking agent of the present invention can be more than 5 mass parts, preferably more than 8 mass parts, relative to 100 mass parts of the polymer. From the viewpoint of preservation stability and prevention of excessive crosslinking, it can be 45 mass parts or less, preferably 40 mass parts or less, and more preferably 30 mass parts or less. By adding the cross-linking agent of the present invention, the photosensitive resin has better film-forming property after curing.

Optionally, in the resin composition, each 100 parts of the heat-resistant resin corresponds to a number of parts of the triazolyl cross-linking agent independently selected from any value or a range value determined by any two of 0.5 parts, 1 part, 5 parts, 8 parts, 10 parts, 15 parts, 20 parts, 25 parts, 30 parts, 35 parts, 40 parts, 45 parts, 50 parts, by mass.

According to a fourth aspect of the present application, there is provided a use of the triazolyl cross-linking agent as described above and/or the triazolyl cross-linking agent obtained by the preparation method as described above as a heat-resistant resin modifier.

Further, the cross-linking agent in the present invention can be used as a heat-resistant resin modifier. The addition of the cross-linking agent can improve the film-forming property of the resin, improve the adhesion of the heat-resistant resin to copper or copper alloy substrate after curing, inhibit the discoloration of the copper or copper alloy substrate, and meanwhile, the resin has better heat resistance and chemical resistance after curing. The heat-resistant resin includes polyimide resin, precursors of polyimide resin such as polyamide acid resin or polyamide acid ester resin, polybenzoxazole resin, polyamide, polyamideimide, polybenzoimidazole, polybenzothiazole, etc. Some active groups in the resin, such as active ester groups or carboxylic acid groups, are prone to react with copper or copper alloy substrates, and copper ions on the surface of the substrate will diffuse into the resin layer, causing discoloration of the substrate, thus affecting the dielectric properties; when the resin is heated and cured, the copper ions that diffuse into the resin layer will cause the resin to oxidize and decompose, and gaps are formed between the resin layer and the substrate, and reduce the adhesion, thus affecting the normal use of the resin. The structure of the triazolyl cross-linker agent of the present invention contains a carbon-carbon double bond, an amide acid or imide ring, and a triazolyl group. On the one hand, an insoluble three-dimensional polymer is formed by cross-linking reaction, which improves chemical resistance and at the same time has good heat resistance. On another hand, the triazolyl group is easy to complex with copper or copper alloy substrate to form stable complexes, which protect the substrate from corrosion by the resin, inhibit the discoloration of the copper or copper alloy substrate, and at the same time, enhance the adhesion between the resin layer and the substrate. On another hand, the cross-linking agent of the present invention is used in resin compositions to form a polymer network by a cross-linking reaction generated by heating, which enhances the film-forming property of the resin and the mechanical strength of the film. In addition, due to the low boiling point of small molecule triazoles or their derivatives, if they are added directly to the resin, they will be lost during the high temperature thermal imidization process, resulting in a reduction of their effective content; instead, the cross-linking agent of the present invention forms a polymer through crosslinking, fixes the triazolyl groups in the polymer network, which promote a better complexation of the triazolyl group with copper or copper alloy substrate, inhibit substrate discoloration, and improve the adhesion between resin and substrate.

Further, the present invention provides a resin composition comprising a heat-resistant resin and a cross-linking agent. The cross-linking agent is a cross-linking agent with the structure shown in formula (1), and the heat-resistant resin includes but is not limited to a positive photosensitive resin; as a preferred type of the positive photosensitive resin, polyimide or its precursor, polybenzoxazole or its precursor can be listed. The triazolyl cross-linking agent of the present invention contains carbon-carbon double bonds and can undergo a thermal crosslinking reaction. The reaction can be a reaction between cross-linking agent molecules, or a crosslinking reaction between the cross-linking agent and other double-bond-containing substances in the resin composition to ultimately obtain a cured resin. The triazolyl cross-linking agent of the present invention can be used in conjunction with at least one other thermal cross-linking agent, such as a bisphenol A-type epoxy resin, a bisphenol F-type epoxy resin, a bisphenol AD-type epoxy resin, a dimethylol urea, a dihydroxymethylethylidene urea, a dihydroxymethylpropylene urea, a trimethylolmelamine, a hexamethylol melamine, etc. The resin composition may also comprise other components, such as photosensitizers, sensitizers, silane coupling agents, etc., which can be adjusted as needed and are not limited herein. The resin-cured film formed by the resin composition after curing can be used as a surface protective layer, an interlayer insulation layer, and a rewiring layer, etc. of a semiconductor device, and is not limited herein.

Beneficial effects that can be produced by the present application include:
1) The cross-linking agent provided in the present application has very good chemical resistance, as well as good heat resistance, and can protect the substrate from corrosion by the resin, inhibit the discoloration of the copper or copper alloy substrate, and at the same time, enhance the adhesion between the resin layer and the substrate;
2) The preparation method of the cross-linking agent provided in the present application has the advantages of easy availability of raw materials, simple process and low cost, which is conducive to industrialized production; due to the cross-linking reaction generated by heating, a polymer network is formed, which enhances the film-forming property of the resin and the mechanical strength of the film.

DETAILED DESCRIPTION OF THE EMBODIMENTS

Several specific embodiments are described below to illustrate the present application, which will be helpful to those of ordinary skill in the art for a fuller understanding, but the present disclosure is not limited to these embodiments. It should be noted that the evaluation of the resin synthesized in the embodiments and the effectiveness evaluation of the prepared resin composition were performed according to the following method.

(1) Molecular Weight Testing

The weight average molecular weight (Mw) of the resin was determined by gel permeation chromatography (instrument model LC-20AD, Shimadzu, Japan) through standard polystyrene conversion, and the eluting solvent was N-methylpyrrolidone.

(2) Viscosity Test

Viscosity test was performed on the resin composition at 25±0.1° C. using a rotational viscometer (Brookfield DV2T RV).

(3) Infrared Testing

The synthesized cross-linking agent samples were tested using a FTIR spectrometer (Tensor-27, Bruker, Germany) to detect the successful preparation of the cross-linking agent of the present application. The cross-linking agent shown in formulae (1-2) and (1-4) above was tested by detecting the infrared absorption peaks of the C—O group and the C—N group in —CO—NH—, and the cross-linking agent shown in formulae (1-1) and (1-3) was tested by detecting the infrared absorption peaks of the C=O and the C—N groups in the imide ring, to determine the successful preparation of the cross-linking agent.

(4) Film-Forming Property

A sample of the resin composition was uniformly coated onto a silicon wafer and then placed on a heating table (HT-300 experimental electric heating plate, Guangzhou Gdana Instrument Co., Ltd.) at 120° C. for 3 minutes of soft baking to obtain a resin film with a film thickness of 10~20 μm. The film was then placed in a vacuum oxygen-free oven (MOLZK-32D1), and heat-treated at 170° C. for 30 minutes under nitrogen atmosphere protection; after 1 hour of heating up to 320° C., the film was treated at 320° C. for another 1 hour, followed by natural cooling directly in the oven to below 50° C., to ultimately obtain the cured film. The silicon wafers with cured film were placed in hydrofluoric acid solution to subject to corrosion and film detachment. The film-forming property was evaluated using the following criteria.
"Excellent" (E): The resin composition can form a film, has toughness, and does not break when folded in half;
"Good" (G): The resin composition can form a film, has toughness, but break when folded in half;
"Poor" (P): The resin composition cannot form a film and appears in fragmented form.
If the film-forming property is "Poor", the chemical resistance test is not evaluated.

(5) Adhesion Test of Resin-Cured Film and Copper Substrate

A sample of the resin composition was uniformly coated onto a copper substrate using a spin coater and then placed on a heating table (HT-300 experimental electric heating plate, Guangzhou Gdana Instrument Co., Ltd.) at 120° C. for 3 minutes of soft baking to obtain a resin film with a film thickness of 10~20 μm. The resin film was inscribed with 10 rows×10 columns of squares using a gridder (BYK-Gardner A-5125), then placed in a vacuum oxygen-free oven (MOLZK-32D1), and heat-treated at 170° C. for 30 minutes under nitrogen atmosphere protection; after 1 hour of heating up to 320° C., the film was treated at 320° C. for another 1 hour, followed by natural cooling directly in the oven to below 50° C., to ultimately obtain the cured film. Finally, the peel test was carried out with adhesive tape (3M adhesive tape) with reference to the national standard GB/T 9286-1998 Scratching Test for Color Paint Film and Varnish Film, and the number of frames peeled off was recorded as the peeling situation before the PCT test.

"a" indicates no stripping; "b" indicates stripping greater than or equal to 1.

The cured film obtained by the same method described above is placed in a PCT test chamber for 120 hours of PCT aging test (121° C., 2 atmospheres of saturated steam; Dongguan Hongjin Technology PCT-30), and after the PCT test was completed, the peeling test was performed again using the tape in the same way as described above, and the number of cells peeled off was recorded as the peeling condition after the PCT test., the same method as above is used to conduct a peel test using adhesive tape, and the number of frames peeled off was recorded as the peeling situation after the PCT test.

If the number of pieces peeled off in the adhesion peel test is less than 5, it is regarded as "Excellent" (E), if it is less than 10, it is regarded as "Good" (G), and if it is more than or equal to 10, it is regarded as "Poor" (P).

(6) Copper Discoloration Test

The resin composition was uniformly coated onto a copper substrate, and then placed on a heating table at 120° C. for 3 minutes for soft baking to obtain a resin film with a film thickness of 10 to 20 μm, and after being left at room temperature for 12 h, the film was placed in a developer solution to dissolve the resin film. The discoloration of the copper substrate after resin film dissolution was evaluated according to the following criteria.

"Best" (B): Discoloration of the copper substrate is not confirmed even when observed visually with a 200× optical microscope;

"Good" (G): Discoloration of the copper substrate is not confirmed under visual inspection, but confirmed when observed with a 200× optical microscope;

"Slightly good" (S): Discoloration of the copper substrate is confirmed under visual inspection;

"Poor" (P): Severe discoloration of the copper substrate is confirmed under visual inspection.

(7) Heat Resistance

A sample of the resin composition was uniformly coated onto a silicon wafer using a spin coater and then placed on a heating table (HT-300 experimental electric heating plate, Guangzhou Gdana Instrument Co., Ltd.) at 120° C. for 3 minutes of soft baking to obtain a resin film with a film thickness of 10~20 μm. The film was then placed in a vacuum oxygen-free oven (MOLZK-32D1), and heat-treated at 170° C. for 30 minutes under nitrogen atmosphere protection; after 1 hour of heating up to 320° C., the film was treated at 320° C. for another 1 hour, followed by natural cooling directly in the oven to below 50° C., to ultimately obtain the cured film.

The heat resistance of the resin was evaluated by determining the temperature at which the weight of the cured film described above was reduced by 5% (i.e., $T_{5\ wt\ \%}$). The test was conducted using a thermogravimetric analyzer (TA, USA, Q50 series), temperature increase rate: 10° C./min, temperature range 30~650° C.

(8) Chemical Resistance

A sample of the resin composition was uniformly coated onto a silicon wafer using a spin coater and then placed on a heating table (HT-300 experimental electric heating plate, Guangzhou Gdana Instrument Co., Ltd.) at 120° C. for 3 minutes of soft baking to obtain a resin film with a film thickness of 10~20 μm. The film was then placed in a vacuum oxygen-free oven (MOLZK-32D1), and heat-treated at 170° C. for 30 minutes under nitrogen atmosphere protection; after 1 hour of heating up to 320° C., the film was treated at 320° C. for another 1 hour, followed by natural cooling directly in the oven to below 50° C., to ultimately obtain the cured film. The cured films were immersed in 10 wt % sodium hydroxide (NaOH) aqueous solution, 10 vol % sulfuric acid aqueous solution, and N-methylpyrrolidone (NMP) at 50° C. for 30 min, respectively, and observed for cracks. The cracking of the films was evaluated based on the following criteria:

"None" (N): no cracks;

"Slight" (S1): slight cracks can be observed;

"Severe" (Se): large number of cracks, or even the film breaks into pieces.

In this application, BANI-X (Maruzen Petrochemical Co., Ltd.) is compared to the cross-linking agent of the present application, and the structure of the BANI-X is shown below:

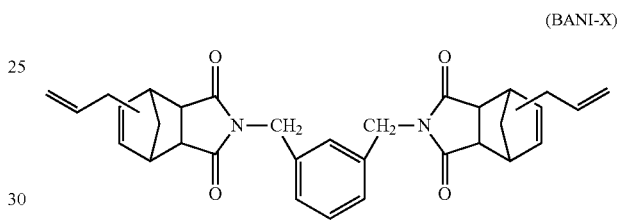

(BANI-X)

Example 1

Synthesis of Cross-Linking Agent A-1:

To a 500 ml three-necked flask equipped with a stirrer and a thermometer, 250 ml of solvent N-methylpyrrolidone (NMP), 9.91 g of 3,5-diamino-1,2,4-triazole (0.1mol, Aladdin Reagent) were added sequentially, start stirring, and after 3,5-diamino-1,2,4-triazole was fully dissolved, 28.03 g of allyl succinic anhydride (0.2 mol, Aladdin Reagent) was added slowly; after the addition was completed, the reaction was continued for 20 h at 50° C. and the reaction is complete; the obtained reaction solution was poured into deionized water, the precipitated product was collected by filtration and washed with deionized water for three times, and then dried in vacuum at 40° C. to obtain the cross-linking agent A-1.

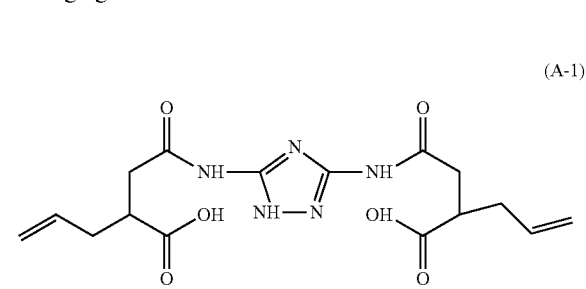

(A-1)

The structural formula of the obtained cross-linking agent A-1 is shown in Formula (A-1) and the IR information is as follows:

FT-IR: 1648 cm$^{-1}$ for C—O symmetric stretching vibration of CONH and 1550 cm$^{-1}$ for C—N asymmetric stretching vibration of CO—NH.

Example 2

Synthesis of Cross-Linking Agent A-2:

To a 500 ml three-necked flask equipped with a stirrer and a thermometer, 250 ml of NMP, 9.91 g of 3,5-diamino-1,2,4-triazole (0.1 mol, Aladdin Reagent) were added sequentially, start stirring, and after 3,5-diamino-1,2,4-triazole was fully dissolved, 28.03 g of allyl succinic anhydride (0.2 mol, Aladdin Reagent) was added slowly; after the addition was completed, the reaction was continued for 20 h at 50° C., then 31.6 g of pyridine (0.4 mol) was added to the reaction system, stirred well and 40.84 g of acetic anhydride (0.4 mol) was added slowly, reacted for 20 h at 25° C. and the reaction is complete; the obtained reaction solution was poured into deionized water, the precipitated product was collected by filtration and washed with deionized water for three times, and then dried in vacuum at 40° C. to obtain the purified cross-linking agent A-2.

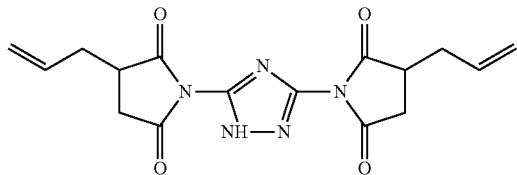

(A-2)

The structural formula of the obtained cross-linking agent A-2 is shown in Formula (A-2) and the IR information is as follows:

FT-IR: 1780 cm$^{-1}$ and 1720 cm$^{-1}$ for asymmetric and symmetric stretching of C=O on the imide ring, respectively, 725 cm$^{-1}$ for C—O bending vibration on the imide ring, and 1373 cm$^{-1}$ for C—N stretching vibration on the imide ring.

Example 3

Synthesis of Cross-Linking Agent A-3:

To a 500 ml three-necked flask equipped with a stirrer and a thermometer, 250 ml of NMP, 9.91 g of 3,5-diamino-1,2,4-triazole (0.1 mol, Aladdin Reagent) were added sequentially, start stirring, and after 3,5-diamino-1,2,4-triazole was fully dissolved, 22.40 g of itaconic anhydride (0.2 mol, Zhejiang Guoguang Biochemical Co., Ltd) was added slowly; after the addition was completed, the reaction was continued for 20 h at 50° C. and the reaction is complete; the obtained reaction solution was poured into deionized water, the precipitated product was collected by filtration and washed with deionized water for three times, and then dried in vacuum at 40° C. to obtain the cross-linking agent A-3.

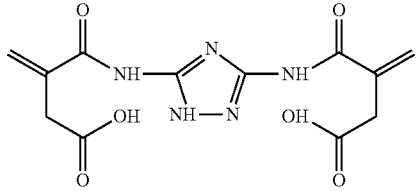

(A-3)

The structural formula of the obtained cross-linking agent A-3 is shown in Formula (A-3) and the IR information is as follows:

FT-IR: 1645 cm$^{-1}$ for C—O symmetric stretching vibration of CONH and 1540 cm$^{-1}$ for C—N asymmetric stretching vibration of CO—NH.

Example 4

Synthesis of Cross-Linking Agent A-4:

To a 500 ml three-necked flask equipped with a stirrer and a thermometer, 250 ml of NMP, 9.91 g of 3,5-diamino-1,2,4-triazole (0.1 mol, Aladdin Reagent) were added sequentially, start stirring, and after 3,5-diamino-1,2,4-triazole was fully dissolved, 22.40 g of itaconic anhydride (0.2mol, Zhejiang Guoguang Biochemical Co., Ltd) was added slowly; after the addition was completed, the reaction was continued for 20 h at 50° C., then 31.6 g of pyridine (0.4 mol) was added to the reaction system, stirred well and 40.84 g of acetic anhydride (0.4 mol) was added slowly, reacted for 20 h at 25° C. and the reaction is complete; the obtained reaction solution was poured into deionized water, the precipitated product was collected by filtration and washed with deionized water for three times, and then dried in vacuum at 40° C. to obtain the purified cross-linking agent A-4.

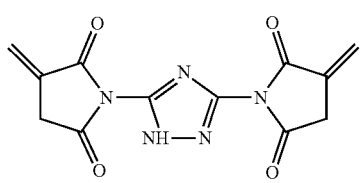

(A-4)

The structural formula of the obtained cross-linking agent A-4 is shown in Formula (A-4) and the IR information is as follows:

FT-IR: 1774 cm$^{-1}$ and 1720 cm$^{-1}$ for asymmetric and symmetric stretching of C=O on the imide ring, respectively, 725 cm$^{-1}$ for C=O bending vibration on the imide ring, and 1370 cm$^{-1}$ for C—N stretching vibration on the imide ring.

Example 5

Synthesis of Cross-Linking Agent A-5:

To a 500 ml three-necked flask equipped with a stirrer and a thermometer, 250 ml of NMP, 9.91 g of 3,5-diamino-1,2,4-triazole (0.1 mol, Aladdin Reagent) were added sequentially, start stirring, and after 3,5-diamino-1,2,4-triazole was fully dissolved, 19.60 g of maleic anhydride (0.2 mol, Zibo Qixiang Tengda Chemical Co., Ltd) was added slowly; after the addition was completed, the reaction was continued for 20 h at 50° C. and the reaction is complete; the obtained reaction solution was poured into deionized water, the precipitated product was collected by filtration and washed with deionized water for three times, and then dried in vacuum at 40° C. to obtain the cross-linking agent A-5.

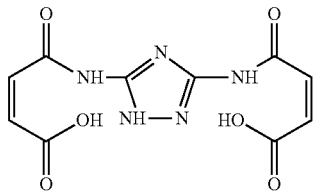

(A-5)

The structural formula of the obtained cross-linking agent A-5 is shown in Formula (A-5) and the IR information is as follows:

FT-IR: 1650 cm$^{-1}$ for C—O symmetric stretching vibration of CONH and 1550 cm$^{-1}$ for C—N asymmetric stretching vibration of CO—NH.

Example 6

Synthesis of Cross-Linking Agent A-6:

To a 500 ml three-necked flask equipped with a stirrer and a thermometer, 250 ml of NMP, 9.91 g of 3,5-diamino-1,2,4-triazole (0.1 mol, Aladdin Reagent) were added sequentially, start stirring, and after 3,5-diamino-1,2,4-triazole was fully dissolved, 19.60 g of maleic anhydride (0.2 mol, Zibo Qixiang Tengda Chemical Co., Ltd) was added slowly; after the addition was completed, the reaction was continued for 20 h at 50° C., then 31.6 g of pyridine (0.4 mol) was added to the reaction system, stirred well and 40.84 g of acetic anhydride (0.4 mol) was added slowly, reacted for 20 h at 25° C. and the reaction is complete; the obtained reaction solution was poured into deionized water, the precipitated product was collected by filtration and washed with deionized water for three times, and then dried in vacuum at 40° C. to obtain the purified cross-linking agent A-6.

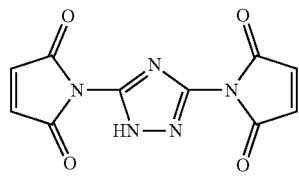

(A-6)

The structural formula of the obtained cross-linking agent A-6 is shown in Formula (A-6) and the IR information is as follows:

FT-IR: 1780 cm$^{-1}$ and 1720 cm$^{-1}$ for asymmetric and symmetric stretching of C=O on the imide ring, respectively, 723 cm$^{-1}$ for C=O bending vibration on the imide ring, and 1373 cm$^{-1}$ for C—N stretching vibration on the imide ring.

Example 7

Synthesis of Cross-Linking Agent A-7:

To a 500 ml three-necked flask equipped with a stirrer and a thermometer, 250 ml of NMP, 9.91 g of 3,5-diamino-1,2,4-triazole (0.1 mol, Aladdin Reagent) were added sequentially, start stirring, and after 3,5-diamino-1,2,4-triazole was fully dissolved, 40.85 g of 5-allyl nadic anhydride (0.2 mol, Puyang Huicheng Electronic Materials Co., Ltd) was added slowly; after the addition was completed, the reaction was continued for 20 h at 50° C. and the reaction is complete; the obtained reaction solution was poured into deionized water, the precipitated product was collected by filtration and washed with deionized water for three times, and then dried in vacuum at 40° C. to obtain the cross-linking agent A-7.

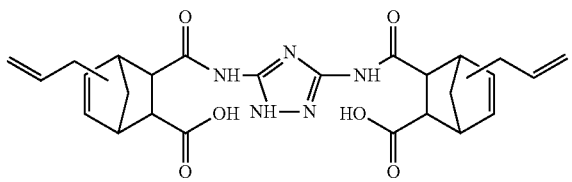

(A-7)

The structural formula of the obtained cross-linking agent A-7 is shown in Formula (A-7) and the IR information is as follows:

FT-IR: 1643 cm$^{-1}$ for C=O symmetric stretching vibration of CONH and 1550 cm$^{-1}$ for C—N asymmetric stretching vibration of CO—H.

Example 8

Synthesis of Cross-Linking Agent A-8:

To a 500 ml three-necked flask equipped with a stirrer and a thermometer, 250 ml of NMP, 9.91 g of 3,5-diamino-1,2,4-triazole (0.1 mol, Aladdin Reagent) were added sequentially, start stirring, and after 3,5-diamino-1,2,4-triazole was fully dissolved, 40.85 g of 5-allyl nadic anhydride (0.2 mol, Puyang Huicheng Electronic Materials Co., Ltd) was added slowly; after the addition was completed, the reaction was continued for 20 h at 50° C., then 31.6 g of pyridine (0.4 mol) was added to the reaction system, stirred well and 40.84 g of acetic anhydride (0.4 mol) was added slowly, reacted for 20 h at 25° C. and the reaction is complete; the obtained reaction solution was poured into deionized water, the precipitated product was collected by filtration and washed with deionized water for three times, and then dried in vacuum at 40° C. to obtain the purified cross-linking agent A-8.

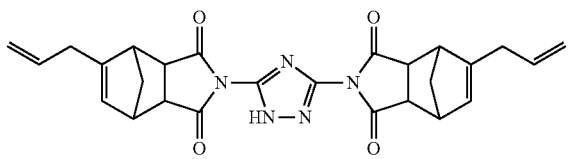

(A-8)

The structural formula of the obtained cross-linking agent A-8 is shown in Formula (A-8) and the IR information is as follows:

FT-IR: 1780 cm$^{-1}$ and 1720 cm$^{-1}$ for asymmetric and symmetric stretching of C=O on the imide ring, respectively, 725 cm 1 for C=O bending vibration on the imide ring, and 1373 cm$^{-1}$ for C—N stretching vibration on the imide ring.

Example 9

Synthesis of Diamine Monomer B:

To a 500 ml three-necked flask equipped with a stirrer and a thermometer, 250 ml of NMP, 19.82 g of 3,5-diamino-1,2,4-triazole (0.2 mol, Aladdin Reagent) were added sequentially, stirred and dissolved; after 3,5-diamino-1,2,4-triazole was fully dissolved, the temperature was raised to 80° C., and 21.81 g of pyromellitic dianhydride (0.1 mol, Aladdin Reagent) was added slowly; the reaction was continued for 12 h at 80° C. followed by 20 h at room temperature, then 31.6 g of pyridine (0.4 mol) was added to the reaction system, stirred well and 40.84 g of acetic anhydride (0.4 mol) was added slowly, the reaction was continued for 20 h at room temperature and the reaction is complete; the obtained reaction solution was poured into deionized water, filtered to collect the precipitate, and the precipitate obtained was filtered out and washed with deionized water for three times, and then dried in vacuum at 50° C. for 72 h to obtain the diamine monomer B.

Synthesis of Cross-Linking Agent A-9:

To a 500 ml three-necked flask equipped with a stirrer and a thermometer, 250 ml of NMP, 38.03 g of the diamine monomer B (0.1 mol) were added sequentially, start stirring, and after the diamine monomer B was fully dissolved, 40.85 g of 5-allyl nadic anhydride (0.2 mol, Puyang Huicheng Electronic Materials Co., Ltd) was added slowly; after the addition was completed, the reaction was continued for 20 h at 50° C., then 31.6 g of pyridine (0.4 mol) was added to the reaction system, stirred well and 40.84 g of acetic anhydride (0.4 mol) was added slowly, reacted for 20 h at 25° C. and the reaction is complete; the obtained reaction solution was poured into deionized water, the precipitated product was collected by filtration and washed with deionized water for three times, and then dried in vacuum at 40° C. to obtain the purified cross-linking agent A-9.

continued for 20 h at room temperature and the reaction is complete; the obtained reaction solution was poured into deionized water, filtered to collect the precipitate, and the precipitate obtained was filtered out and washed with deionized water for three times, and then dried in vacuum at 50° C. for 72 h to obtain the diamine monomer C.

Synthesis of Cross-Linking Agent A-10:

To a 500 ml three-necked flask equipped with a stirrer and a thermometer, 250 ml of NMP, 47.24 g of the diamine monomer C (0.1 mol) were added sequentially, start stirring, and after the diamine monomer C was fully dissolved, 40.85 g of 5-allyl nadic anhydride (0.2 mol, Puyang Huicheng Electronic Materials Co., Ltd) was added slowly; after the addition was completed, the reaction was continued for 20 h at 50° C. and the reaction is complete; the obtained

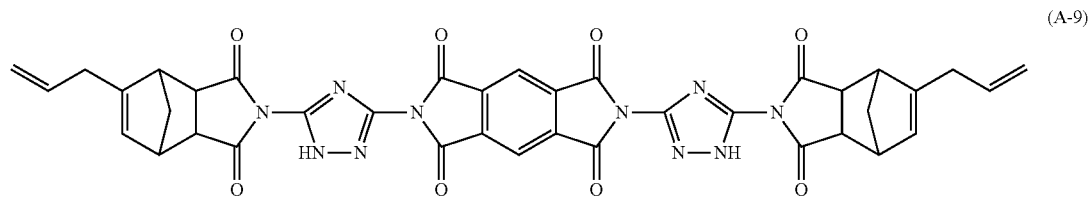 [SMILES: C=CCC1=CC2CC1C1C(=O)N(c3nc(-n4c(=O)c5cc6c(=O)n(-c7n[nH]c(N8C(=O)C9C%10C=C(CC=C)C(C%10)C9C8=O)n7)c(=O)c6cc5c4=O)n[nH]3)C(=O)C21]

(A-9)

The structural formula of the obtained cross-linking agent A-9 is shown in Formula (A-9) and the IR information is as follows:

FT-IR: 1778 cm$^{-1}$ and 1718 cm$^{-1}$ for asymmetric and symmetric stretching of C=O on the imide ring, respecreaction solution was poured into deionized water, the precipitated product was collected by filtration and washed with deionized water for three times, and then dried in vacuum at 40° C. to obtain the purified cross-linking agent A-10.

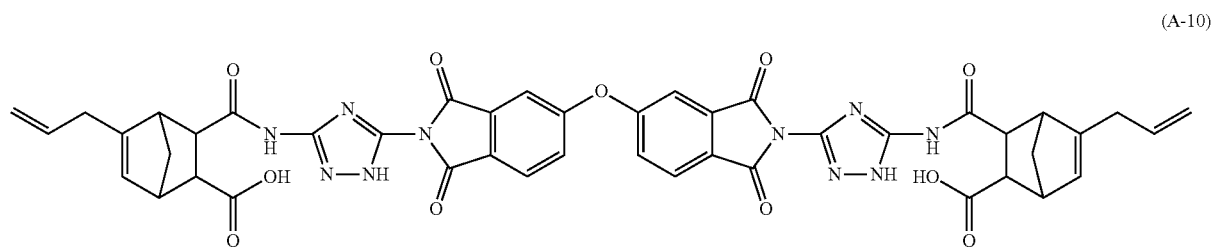 [SMILES: C=CCC1=CC2CC1C(C(=O)Nc1n[nH]c(N3C(=O)c4ccc(Oc5ccc6c(c5)C(=O)N(c5n[nH]c(NC(=O)C7C8CC(C=C8CC=C)C7C(=O)O)n5)C6=O)cc4C3=O)n1)C2C(=O)O]

(A-10)

tively, 726 cm$^{-1}$ for C=O bending vibration on the imide ring, and 1369 cm$^{-1}$ for C—N stretching vibration on the imide ring.

Example 10

Synthesis of Diamine Monomer C:

To a 500 ml three-necked flask equipped with a stirrer and a thermometer, 250 ml of NMP, 20.81 g of 3,5-diamino-1,2,4-triazole (0.21 mol, Aladdin Reagent) were added sequentially, stirred and dissolved; after 3,5-diamino-1,2,4-triazole was fully dissolved, the temperature was raised to 80° C., and 31.02 g of 4,4'-Oxydiphthalic anhydride (0.1 mol, Aladdin Reagent) was added slowly; the reaction was continued for 12 h at 80° C. followed by 20 h at room temperature, then 31.6 g of pyridine (0.4 mol) was added to the reaction system, stirred well and 40.84 g of acetic anhydride (0.4 mol) was added slowly, the reaction was The structural formula of the obtained cross-linking agent A-10 is shown in Formula (A-10) and the IR information is as follows:

FT-IR: 1643 cm$^{-1}$ for C=O symmetric stretching vibration of CONH, 1550 cm$^{-1}$ for C—N asymmetric stretching vibration of CONH, and 1778 cm$^{-1}$ and 1718 cm$^{-1}$ for asymmetric and symmetric stretching of C=O on the imide ring, respectively.

Preparation of Resin Compositions

Reference Example 1

Synthesis of Polyimide Precursors:

Under nitrogen flow, 31.00 g (0.10 mol) of 2,3,3',4'-diphenyl ether tetracarboxylic acid dianhydride (ODPA), 0.07 g (0.0007 mol) of triethylamine, 15 g (0.202 mol) of n-butanol, and 100 g of NMP were added sequentially to a 500 ml three-necked flask, dissolved with stirring, and reacted for 24 h at 25° C. Then 24.05 g (0.202 mol) of sulfoxide chloride was added dropwise, and the temperature of the reaction system was ensured to be controlled below 0° C. during the dropwise addition. After the dropwise addition was completed, the reaction was continued at low temperature (0° C.) for 3 h to obtain a solution of di-n-butyl 2,3,3',4'-diphenyl ether tetracarboxylate acyl chloride.

Under nitrogen flow, 36.57 g (0.10 mol) of 2,2-bis (3-amino-4-hydroxyphenyl) hexafluoropropane (BAHF) was weighed and added into a 500 ml three-necked flask, and then 100 g of NMP, 28 g of pyridine (0.35 mol) were added sequentially with stirring to dissolve; the reaction system was cooled down to below 0° C., and then the solution of di-n-butyl 2,3,3',4'-diphenyl ether tetracarboxylate acyl chloride was added slowly by dripping, and the temperature of the reaction system was controlled to be below 0° C. during the dripping. After dripping, continue the reaction at low temperature (0° C.) for 3 hours and the reaction is complete. The polymer solution was poured into 3 L of deionized water and a white polymer precipitate was precipitated. It was filtered, then washed three times with deionized water, and dried under vacuum at 80° C. for 48 h to obtain polyimide precursor C, i.e., polyamide acid ester resin. The molecular weight of the polymers was determined by gel permeation chromatography (standard polystyrene conversion), and the weight average molecular weight (Mw) were in the range of 20 to 23 thousand.

Preparation of Resin Compositions:

In a three-necked flask equipped with stirring, 10.0 g of the synthesized polyamide acid ester resin C was dissolved in 20 g of NMP, after sufficient dissolution, 0.3 g of silane coupling agent 3-ureidopropyltriethoxysilane (A-1160, Shin-Etsu Chemical) was added, and then 0.5 g of the cross-linking agent A-1 obtained in Example 1 was added; after sufficient dissolution, the resin composition was obtained by press-filtration using a 1.0 μm filter membrane with a viscosity of 3100cp measured at 25° C.

Reference Example 2 The same as Reference Example 1 except that the cross-linking agent A-1 was changed from 0.5 g to 0.8 g.

Reference Example 3 The same as Reference Example 1 except that the cross-linking agent A-1 was changed from 0.5 g to 1.0g.

Reference Example 4 The same as Reference Example 1 except that the cross-linking agent A-1 was changed from 0.5 g to 1.3g.

Reference Example 5 The same as Reference Example 2 except that the cross-linking agent A-1 is replaced with A-2.

Reference Example 6 The same as Reference Example 2 except that the cross-linking agent A-1 is replaced with A-3.

Reference Example 7 The same as Reference Example 2 except that the cross-linking agent A-1 is replaced with A-4.

Reference Example 8 The same as Reference Example 2 except that the cross-linking agent A-1 is replaced with A-5.

Reference Example 9 The same as Reference Example 2 except that the cross-linking agent A-1 is replaced with A-6.

Reference Example 10 The same as Reference Example 2 except that the cross-linking agent A-1 is replaced with A-7.

Reference Example 11 The same as Reference Example 2 except that the cross-linking agent A-1 is replaced with A-8.

Reference Example 12 The same as Reference Example 2 except that the cross-linking agent A-1 is replaced with A-9.

Reference Example 13 The same as Reference Example 2 except that the cross-linking agent A-1 is replaced with A-10.

Comparative Example 1 The same as Reference Example 2 except that the cross-linking agent A-1 is replaced with BANI-X (Maruzen Petrochemical Co., Ltd.).

Comparative Example 2 The same as Reference Example 2 except that the cross-linking agent A-1 is replaced with BANI-X (Maruzen Petrochemical Co., Ltd.), in addition to adding 0.20 g of benzotriazole (Aladdin Reagent) to the system.

Comparative Example 3 The same as Reference Example 2 except that the cross-linking agent A-1 is replaced with BANI-X (Maruzen Petrochemical Co., Ltd.), in addition to adding 0.35 g of benzotriazole (Aladdin Reagent) to the system.

Comparative Example 4 The same as Reference Example 2 except that the cross-linking agent A-1 is replaced with BANI-X (Maruzen Petrochemical Co., Ltd.), in addition to adding 0.12 g of 1H-1,2,4-triazole (Merck& Co.) to the system.

Comparative Example 5 The same as Reference Example 2 except that the cross-linking agent A-1 is replaced with BANI-X (Maruzen Petrochemical Co., Ltd.), in addition to adding 0.20 g of 1H-1,2,4-triazole (Merck& Co.) to the system.

Comparative Example 6 The same as Reference Example 2 except that the cross-linking agent A-1 is replaced with 2,6-Dimethoxymethylene-4-tert-butylphenol (DMOM-PTBP-MF, Honshu Chemical).

Comparative Example 7 The same as Reference Example 2 except that the cross-linking agent A-1 is replaced with 2,6-Dimethoxymethylene-4-tert-butylphenol (DMOM-PTBP-MF, Honshu Chemical), in addition to adding 0.35 g of benzotriazole (Aladdin Reagent) to the system.

Comparative Example 8 The same as Reference Example 1 except that no cross-linking agent was added.

The resin compositions prepared as described above were evaluated in accordance with the previously described adhesion test, copper discoloration test, heat resistance, and chemical resistance test, respectively, and the results of each reference example are shown in Table 1; the results of each comparative example are shown in Table 2.

As can be seen from the table, the resin compositions with the addition of the cross-linking agent A-1 to A-10 of the present application have better film-forming properties, the resin-cured film has good adhesion with the copper substrate, and there is no or a small amount of peeling in the adhesion test; In the copper discoloration test, there is a good inhibition of copper substrate discoloration. In chemical resistance test, the resin-cured film did not crack in strong acid solution, strong alkali solution, or organic solvent. The resin-cured film with the addition of the cross-linking agent of the present application still maintains good heat resistance, and its $T_{5\ wt\ \%}$ is comparable to that of the pure resin-cured film.

As can be seen from Comparative Examples 1 to 5, when only BANI-X is added to the resin composition, the adhesion of the cured film to the copper substrate is poor, and the discoloration of the copper substrate is serious, and when small-molecule triazoles are further added to the composition in a small amount (in Comparative Examples 2 and 4, the effective content of the added triazoles is comparable to that of Reference Example 11 of the present application), the adhesion and the inhibition of copper discoloration did not achieve the best results of the present application, and an increase in the amount of addition can achieves the same adhesion effect and inhibitory effect on copper discoloration as the present application (in Comparative Examples 3 and 5, the effective content of the added triazole is comparable to that of Reference Example 7 with the highest content of triazole in the reference examples of the present application), however, after adding so many small molecule triazole compounds, the volatilization of small molecule compounds will lead to a decrease in the thermal stability of the resin, resulting in a decrease in $T_{5\ wt\ \%}$. As can be seen from Comparative Examples 4 to 5, when the commercial cross-linking agent DMOM-PTBP-MF was added to the resin composition without the triazoles, its effect of inhibiting copper discoloration and its adhesion to the substrate was poor; after further addition of higher amounts of benzotriazole, the effect of inhibiting copper discoloration and the adhesion of the cured film to the copper substrate were improved, but its $T_{5\ wt\ \%}$ was decreased.

TABLE 1

| | | Reference Examples | | | | | | | | | | | | |
|---|---|---|---|---|---|---|---|---|---|---|---|---|---|---|
| | | 1 | 2 | 3 | 4 | 5 | 6 | 7 | 8 | 9 | 10 | 11 | 12 | 13 |
| cross-linking agent A-1 | | 0.5 | 0.8 | 1.0 | 1.3 | | | | | | | | | |
| cross-linking agent A-2 | | | | | | 0.8 | | | | | | | | |
| cross-linking agent A-3 | | | | | | | 0.8 | | | | | | | |
| cross-linking agent A-4 | | | | | | | | 0.8 | | | | | | |
| cross-linking agent A-5 | | | | | | | | | 0.8 | | | | | |
| cross-linking agent A-6 | | | | | | | | | | 0.8 | | | | |
| cross-linking agent A-7 | | | | | | | | | | | 0.8 | | | |
| cross-linking agent A-8 | | | | | | | | | | | | 0.8 | | |
| cross-linking agent A-9 | | | | | | | | | | | | | 0.8 | |
| cross-linking agent A-10 | | | | | | | | | | | | | | 0.8 |
| BANI-X | | | | | | | | | | | | | | |
| DMOM-PTBP-MF | | | | | | | | | | | | | | |
| Benzotriazole | | | | | | | | | | | | | | |
| 1H-1,2,4-triazole | | | | | | | | | | | | | | |
| A-1160 | | 0.3 | 0.3 | 0.3 | 0.3 | 0.3 | 0.3 | 0.3 | 0.3 | 0.3 | 0.3 | 0.3 | 0.3 | 0.3 |
| Polyimide precursor C | | 10 | 10 | 10 | 10 | 10 | 10 | 10 | 10 | 10 | 10 | 10 | 10 | 10 |
| Film-forming property | | E | E | E | E | E | E | E | E | E | E | E | E | E |
| film thickness /μm | | 15 | 15 | 15 | 15 | 15 | 15 | 15 | 15 | 15 | 15 | 15 | 15 | 15 |
| Copper discoloration test | | G | B | B | B | B | B | B | B | B | B | B | B | B |
| Adhesion test | Before PCT | a | a | a | a | a | a | a | a | a | a | a | a | a |
| | After PCT | G | E | E | G | E | E | E | E | E | E | E | E | E |
| $T_{5\ wt\ \%}$ (° C.) | | 439 | 435 | 433 | 430 | 435 | 430 | 432 | 436 | 435 | 438 | 440 | 445 | 446 |
| Chemical resistance | 10 wt % NaOH aqueous solution | N | N | N | N | N | N | N | N | N | N | N | N | N |
| | 10 vol % sulfuric acid aqueous solution | N | N | N | N | N | N | N | N | N | N | N | N | N |
| | NMP | N | N | N | N | N | N | N | N | N | N | N | N | N |

TABLE 2

| | | Comparative Example | | | | | | | |
|---|---|---|---|---|---|---|---|---|---|
| | | 1 | 2 | 3 | 4 | 5 | 6 | 7 | 8 |
| cross-linking agent A-1 | | | | | | | | | |
| cross-linking agent A-2 | | | | | | | | | |
| cross-linking agent A-3 | | | | | | | | | |
| cross-linking agent A-4 | | | | | | | | | |
| cross-linking agent A-5 | | | | | | | | | |
| cross-linking agent A-6 | | | | | | | | | |
| cross-linking agent A-7 | | | | | | | | | |
| cross-linking agent A-8 | | | | | | | | | |
| cross-linking agent A-9 | | | | | | | | | |
| BANI-X | | 0.8 | 0.8 | 0.8 | 0.8 | 0.8 | | | |
| DMOM-PTBP-MF | | | | | | | 0.8 | 0.8 | |
| Benzotriazole | | | 0.20 | 0.35 | | | | 0.35 | |
| 1H-1,2,4-triazole | | | | | 0.12 | 0.20 | | | |
| A-1160 | | 0.3 | 0.3 | 0.3 | 0.3 | 0.3 | 0.3 | 0.3 | 0.3 |
| Polyimide precursor C | | 10 | 10 | 10 | 10 | 10 | 10 | 10 | 10 |
| Film-forming property | | E | E | E | E | E | E | E | P |
| film thickness /μm | | 15 | 15 | 15 | 15 | 15 | 15 | 15 | 15 |
| Copper discoloration test | | P | G | B | G | B | P | B | P |
| Adhesion test | Before PCT | b | b | a | b | a | b | a | b |
| | After PCT | P | G | E | G | E | P | E | P |
| $T_{5\ wt\ \%}$ (° C.) | | 440 | 425 | 415 | 422 | 413 | 420 | 400 | 447 |
| Chemical resistance | 10 wt % NaOH aqueous solution | N | N | N | N | N | N | N | — |
| | 10 vol % sulfuric acid aqueous solution | N | N | N | N | N | N | N | — |
| | NMP | N | N | N | | | N | N | — |

The present application designs and synthesizes a triazolyl cross-linking agent by simultaneously introducing a double bond, an amide acid or imide structure, and a triazolyl group into the structure, and by adding it to a resin composition, not only can it improve film-forming properties, improve the adhesion of the resin to the copper or copper alloy substrate after curing, and inhibit the discoloration of the copper or copper alloy substrate, but also the resin has a better heat resistance and chemical resistance after curing. It avoids the poor compatibility caused by too many types of additives, and at the same time alleviate the problem of excessive additives.

The above embodiments are merely some of the embodiments of the present application, and do not limit the present application in any form. Although the present application is disclosed above with the preferred embodiments, the present application is not limited thereto. Some changes or modifications made by any technical personnel familiar with the profession using the technical content disclosed above without departing from the scope of the technical solutions of the present application are equivalent to equivalent implementation cases and fall within the scope of the technical solutions.

What is claimed is:

1. A triazolyl cross-linking agent, wherein the triazolyl cross-linking agent has a general formula described in Formula I:

  Formula I

W is an organic group shown in a general formula (6) or (7):

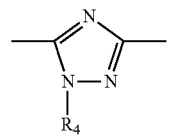 (6)

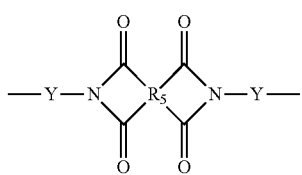 (7)

in the general formula (7), Y represents a structure shown in the general formula (6);

$R_4$ is a hydrogen atom;

a structural formula of $R_5$ is

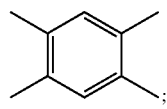

$X_1$ and $X_2$ have the same structure, and are selected from the group consisting of structures described in formulae (2), (3), (4), and (5)

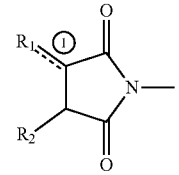 (2)

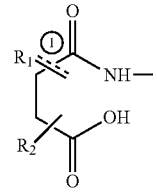 (3)

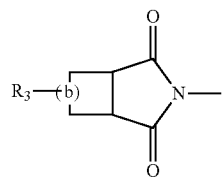 (4)

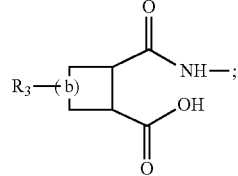 (5)

in the formulae (2) and (3), ==== represents that positions ① is a single bond or a double bond; when it is the single bond, $R_1$ is an alkenyl with a carbon atom number of 2 to 10, and $R_2$ is a hydrogen atom or an alkyl with a carbon atom number of 1 to 6; when it is the double bond, $R_1$ is an alkylidene group with a carbon atom number of 1 to 3, and $R_2$ is a hydrogen atom or an alkyl with a carbon atom number of 1 to 6;

in the formulae (4) and (5), $R_3$ is vinyl, propenyl, allyl, 1-methyl-1-vinyl, 1-buten-4-yl, 1-penten-5-yl, and

has a structural formula of

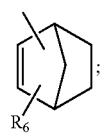

$R_6$ is a hydrogen atom or an alkyl with a carbon atom number of 1 to 6.

2. The triazolyl cross-linking agent according to claim 1, wherein a compound of formula (2) is one selected from the group consisting of formulae (9) and (11);

a compound of formula (3) is one selected from the group consisting of formulae (8) and (10);

a compound of formula (4) is a formula (14);
a compound of formula (5) is a formula (15);

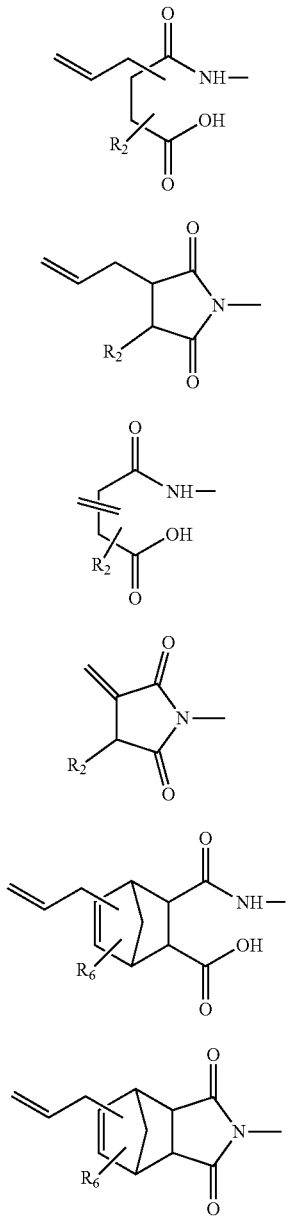

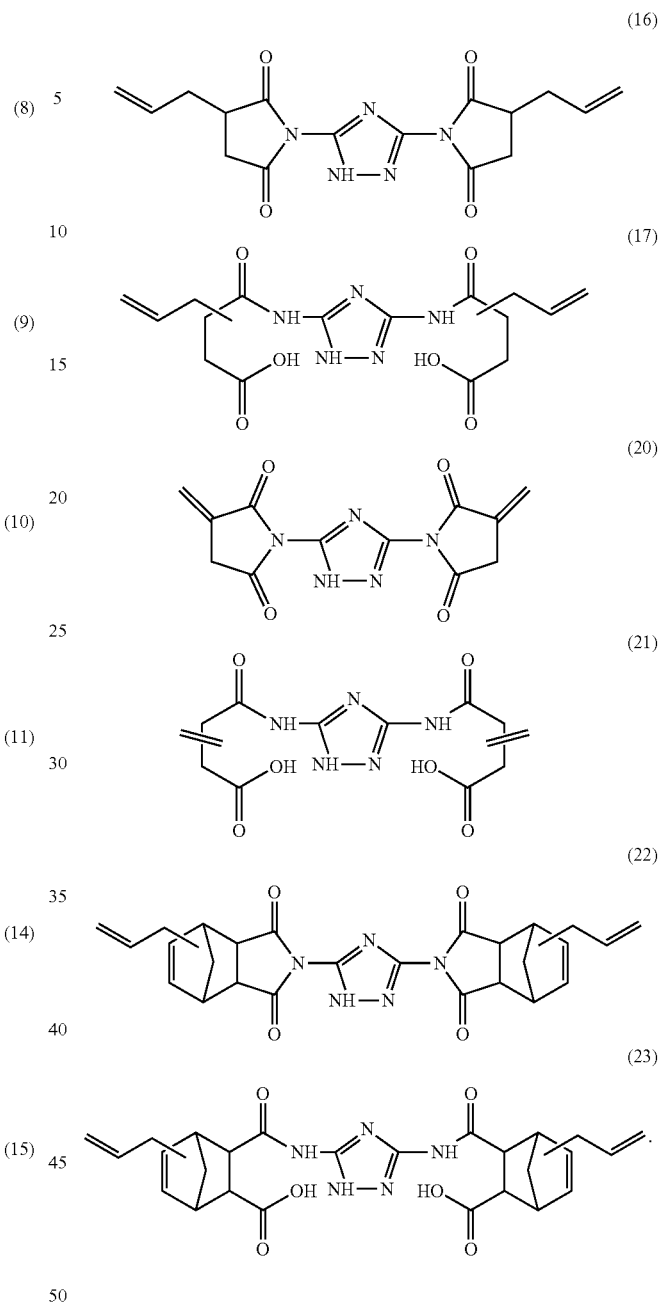

in the formulae (8) to (11), $R_2$ is a hydrogen atom or an alkyl with a carbon atom number of 1 to 6;

in the formulae (14) to (15), $R_6$ is a hydrogen atom or an alkyl with a carbon atom number of 1 to 6.

3. The triazolyl cross-linking agent according to claim 1, wherein a structure of the triazolyl cross-linking agent selected from the group consisting of formulae (16), (17), (20), (21), (22), and (23):

4. A preparation method of the triazolyl cross-linking agent according to claim 1, wherein a reaction step comprises:

performing an amidation reaction between an anhydride monomer of a structure shown in either formula (24) or (25) and a diamine monomer of a structure shown in formula (26) to obtain the triazolyl cross-linking agent; or performing the amidation reaction between the anhydride monomer of the structure shown in either formula (24) or (25) and the diamine monomer of the structure shown in formula (26), followed by an imidization reaction to obtain the triazolyl cross-linking agent;

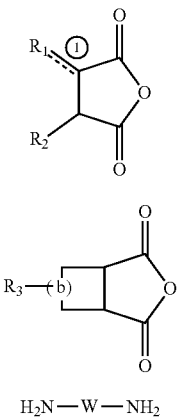

in the formulae (24), (25), and (26), $R_1$, $R_2$, $R_3$, (b), ====, and W are defined as described in claim 1.

5. The preparation method according to claim 4, wherein the amidation reaction and the imidization reaction are carried out in an aprotic polar solvent.

6. The preparation method according to claim 5, wherein the aprotic polar solvent is at least one selected from the group consisting of N-methylpyrrolidone, N,N-dimethylformamide, N,N-dimethylacetamide, dimethylsulfoxide, and γ-butyrolactone.

7. The preparation method according to claim 4, wherein a temperature of the amidation reaction and the imidization reaction is independently in a range from 0° C. to100° C.

8. The preparation method according to claim 4, wherein a temperature of the amidation reaction and the imidization reaction is independently in a range from 20° C. to50° C.

9. The preparation method according to claim 4, wherein a time of the amidation reaction and the imidization reaction is independently in a range from 10 h to 40 h.

10. The preparation method according to claim 4, wherein a time of the amidation reaction and the imidization reaction is independently in a range from 15 h to 30 h.

11. The preparation method according to claim 4, wherein a molar ratio of the anhydride monomer to the diamine monomer is 2: (0.9-1.1).

12. The preparation method according to claim 4, wherein when the amidation reaction followed by the imidization reaction is adopted:
the amidation reaction is followed by adding a base and an anhydride to a reaction solution, and then the imidization reaction is carried out.

13. The preparation method according to claim 12, wherein the base is at least one selected from the group consisting of pyridine, triethylamine, and diisopropylethylamine.

14. The preparation method according to claim 12, wherein the anhydride is at least one selected from the group consisting of acetic anhydride and trifluoroacetic anhydride.

15. A resin composition, wherein the resin composition comprises a heat-resistant resin and a triazolyl cross-linking agent, and the triazolyl cross-linking agent is the triazolyl cross-linking agent according to claim 1.

16. The resin composition according to claim 15, wherein in the resin composition, each 100 parts of the heat-resistant resin corresponds to 0.5 to 50 parts of the triazolyl cross-linking agent by mass.

17. The resin composition according to claim 15, wherein in the resin composition, each 100 parts of the heat-resistant resin corresponds to 5 to 40 parts of the triazolyl cross-linking agent by mass.

18. The resin composition according to claim 15, wherein in the resin composition, each 100 parts of the heat-resistant resin corresponds to 8 to 30 parts of the triazolyl cross-linking agent by mass.

* * * * *